United States Patent [19]
Miyauchi et al.

[11] Patent Number: 6,093,402
[45] Date of Patent: Jul. 25, 2000

[54] PEPTIDES AND HAIR GROWERS HAVING ACTIONS OF PROMOTING PROLIFERATION OF HAIR PAPILLA CELLS

[75] Inventors: Yutaka Miyauchi, 324-10, Shigoka-machi, Takasaki-shi, Gunma-ken, 370-0845; Shigeo Hasegawa, Saitama-ken; Kazuhiko Otoguro; Kanki Komiyama, both of Tokyo, all of Japan

[73] Assignee: Yutaka Miyauchi, Takasaki, Japan

[21] Appl. No.: 09/107,449

[22] Filed: Jun. 30, 1998

[51] Int. Cl.[7] .............................. A01N 65/00; A61K 7/06
[52] U.S. Cl. ........................ 424/195.1; 424/74; 424/880
[58] Field of Search ................... 424/195.1, 74; 514/2, 880

[56] References Cited

FOREIGN PATENT DOCUMENTS

| | | |
|---|---|---|
| 55-31001 | 3/1980 | Japan . |
| 56-166107 | 12/1981 | Japan . |
| 57-6402 | 2/1982 | Japan . |
| 1-20123 | 4/1989 | Japan . |
| 3-227911 | 10/1991 | Japan . |

OTHER PUBLICATIONS

Derwent WPIL Computer Abstract Miyauchi JP09202798, Aug. 5, 1997.

Derwent WPIL Computer Abstract Miyauchi JP09202716, Aug. 5, 1997.

*Primary Examiner*—Herbert J. Lilling
*Attorney, Agent, or Firm*—Arent Fox Kintner Plotkin & Kahn, PLLC

[57] ABSTRACT

Citrus amanatsudaidai peel extract, which was used as a starting materials was purified over various kinds of column chromatography (activated carbon, Amberlite IR-120B [$H^+$], cellulose, Sephadex G25 and HPLC) to isolate a peptide as a white powder. This peptide is a water-soluble neutral substance and shows positive reactions to ninhydrin and sodium nitroprusside and negative reactions to anisaldehyde, phenolsulfuric acid and Dragendorff reagent. Amino acids constituting the peptide of the present invention contain aspartic acid and oxylysine in large amounts. Hair growers containing the peptide of the present invention were successful in promoting 150% proliferation of rabbit hair papilla cells when applied in a concentration of 1.4 $\mu$g/ml.

17 Claims, 2 Drawing Sheets

PEPTIDES AND HAIR GROWERS HAVING ACTIONS OF PROMOTING PROLIFERATION OF HAIR PAPILLA CELLS

BACKGROUND OF THE INVENTION

1. Field of the Invention

The present invention relates to a peptide having actions of promoting proliferation of hair papilla cells and to hair growers having actions of promoting restoration and growth of hair and being effective to prevent loss of hair.

2. Prior Art

While there may be given, as causes of hair loss, factors including reduction in the function of hair follicles under the influence of male hormone, reduction in the metabolic function of hair follicles and hair bulbs, reduction in the physiological function of scalp, local bloodstream disturbance due to strain of scalp, oligotrophy, stress, side effects of drugs, inheritance, etc., the causes of hair loss have not fully been clarified. Accordingly, active ingredients contained in commercially available hair growers act to promote blood circulation in the scalp, to stimulate hair bulbs or to invigorate hair follicles to activate secondarily hair-related cells.

The present applicant found that a mixture of extracts from peels of various kinds of citrus fruits with sake (rice liquor) and an extract of aloe with sake has a hair-growing effect (Japanese Patent Application Laid-open No. Hei 3-227911), but its drug effect has not substantially been clarified yet.

There are demands for hair growers which activate directly hair-related cells based on fundamental studies on the hair growth mechanism and hair loss mechanism In view of such demands, it is an objective of the present invention to provide a peptide acting directly upon hair papilla cells taking charge of the hair growth mechanism to promote proliferation of hair-related cells and also hair growers containing the peptide.

SUMMARY OF THE INVENTION

The present inventors searched widely natural products for physiologically active substances having actions of promoting proliferation of hair papilla cells to find that a novel peptide obtained from extracts of peels and sarcocarps of citrus fruits has such actions.

The peptide according to the present invention has the following physicochemical properties:

(1) Molecular weight: 2,000 to 4,000 (by gel filtration method);

(2) IR absorption spectrum (KBr): as shown in FIG. 1; absorption bands; 3,356, 3,080, 1,676, 1,647, 1,614, 1,500, 1,425, 1,402, 1,358, 1,336, 1,250, 1,151, 1,072 and 985 $cm^{-1}$; UV absorption spectrum (in water) showed no typical absorption peak up to 200 nm;

(3) Solubility: soluble in water, and sparedly or hardly soluble in ether, benzene and chloroform, (4) Color-forming reaction: positive to ninhydrin reaction and to sodium nitroprusside reaction; and negative to anisaldehyde reaction, phenolsulfuric acid reaction and Dragendorff reaction;

(5) Distinction of basic, neutral and acidic properties: neutral;

(6) Property: White crystals or a white crystalline powder developing peculiar odor slightly; and (7) Constituent amino acids: The peptide contains phosphoserine, aspartic acid, serine, glutamic acid, glycine, alanine, valine, cystine, methionine, oxylysine, ornithine, lysine and hystidine in a molar ratio of about 8:9,174:84:4:6:4:4:17:2:13,606:2:1:2, provided that lysine is 1, and it contains oxylysine and aspartic acid in large amounts. The peptide also contains taurine, phosphoethanolamine and urea The peptide of the present invention can be prepared as follows:

Peels of citric fruits such as of citrus amanatsudaidai, citrus iyo (*C. iyo* Hort. Ex Tanaka), citrus hassaku (*C. hassaku* Hort. Ex Tanaka), tangerines or mandarines and lemons are subjected to extraction with an alcohol such as methanol and ethanol, and the extract is filtered. The alcohol in the filtrate obtained is distilled off to obtain a-dry product. The dry product is dissolved in a purified water to prepare an aqueous solution. In the case of sarcoarps of such fruits, they are squeezed to obtain a crude juice. The juice is filtered, and the filtrate is used as a juice solution.

The aqueous solution or juice solution thus obtained is further subjected to adsorption on an ion-exchange resin and the like and elution with an eluent such as dilute ammonia water, followed by concentration of the eluate under reduced pressure to obtain a crude material. The ion-exchange resin can typically be exemplified by Amberlite IR-120B as a strong-acidity cation-exchange resin.

The crude material obtained can be purified by known methods employed conventionally for purification of water-soluble substances, for example, by column chromatography employing a carrier such as activated carbon, cellulose, Sephadec G-25, silica gel and gel filtration or by high-performance liquid chromatography employing an ion-exchange carrier.

The thus obtained peptide is dissolved in water or a hydrous alcohol, and various kinds of components commonly used in hair grooming preparations may, as necessary, added to the resulting solution. The mixture can be employed as a hair grower in the form of hair tonic, shampoo, hair cream or the like. Particularly, a preparation further incorporated with a germicidal component such as an aloe extract is preferred.

Contents of the present invention are not to be limited to the above description, and the objective, advantages, features and uses of the present invention will be understood more clearly by reading the following description with reference to the attached drawings. Further, it should be understood that suitable modifications made without departing from the spirit of the present invention shall all be included within the scope of the present invention.

DETAILED DESCRIPTION OF THE PREFERRED EMBODIMENTS

EXAMPLE 1

Figure 1:
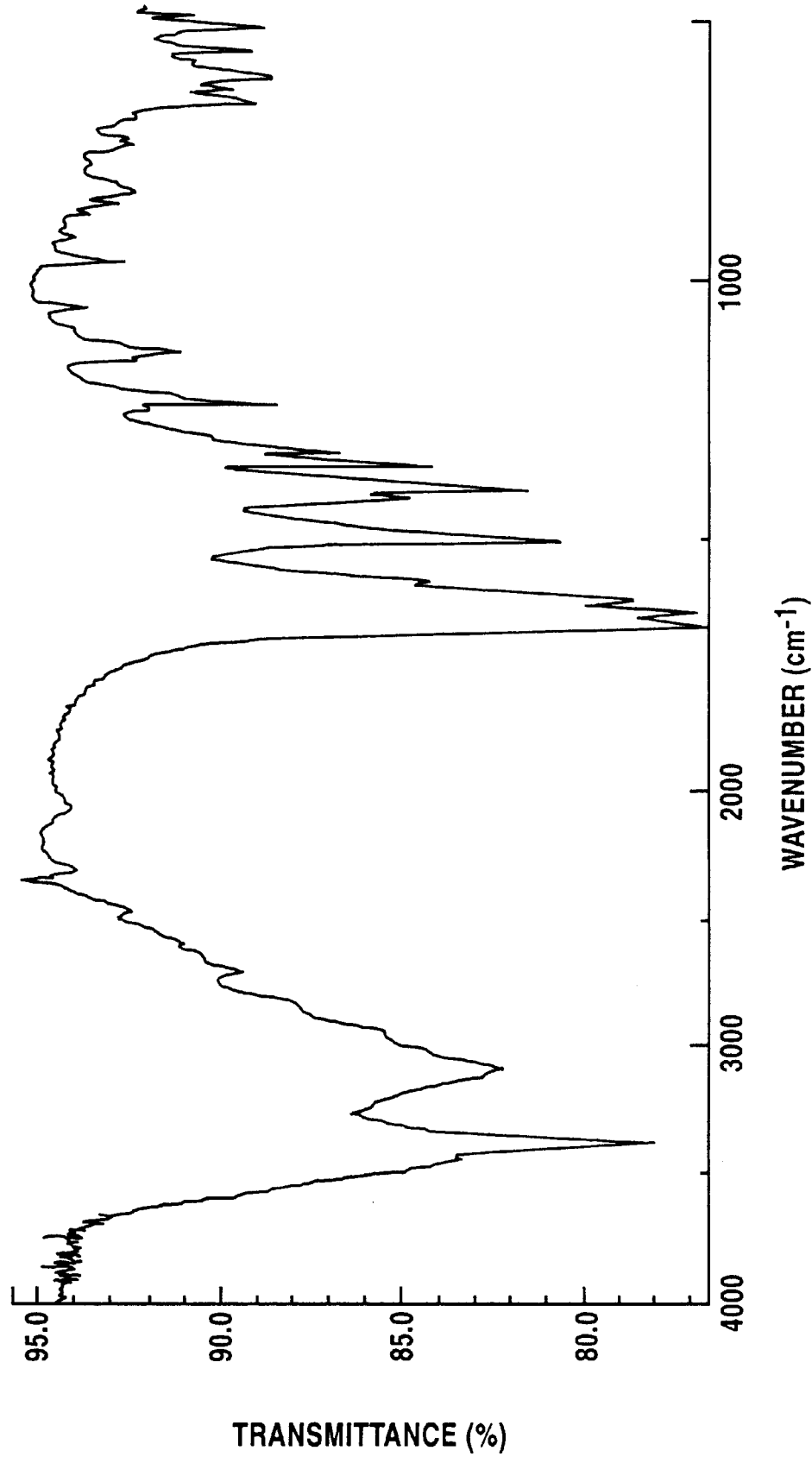
FIG. 1 shows an IR absorption spectrum of the peptide according to the present invention.
Figure 2:
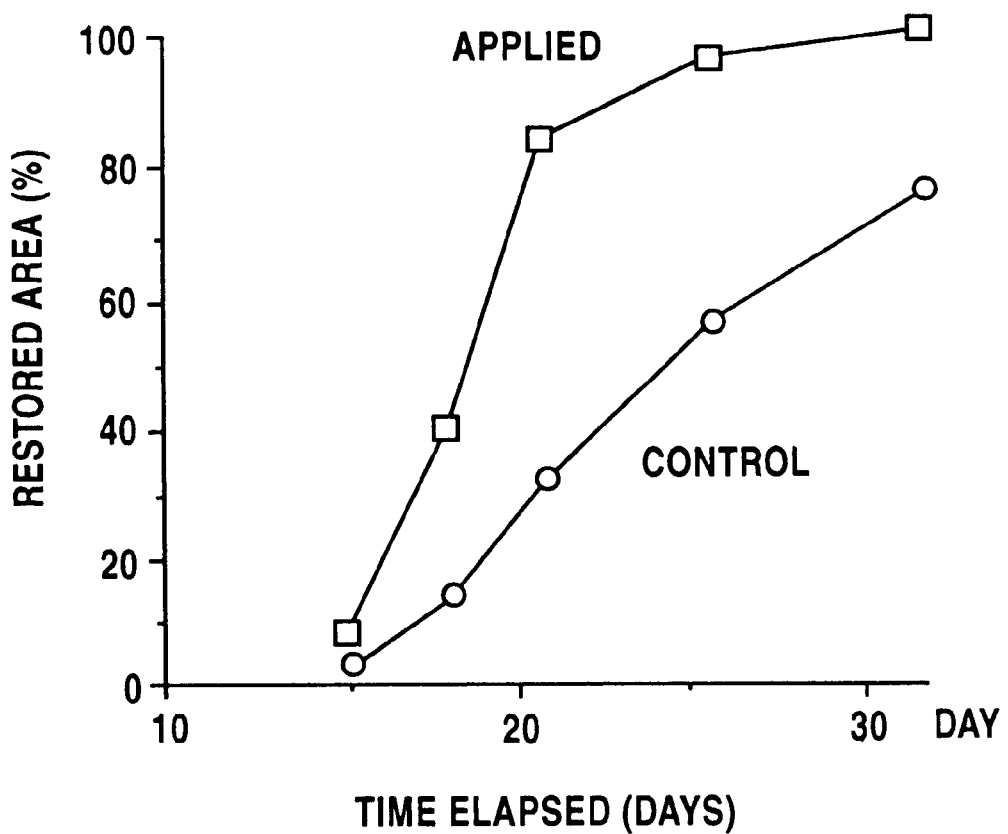
FIG. 2 shows results of hair restoration test in mice.

To finely-chopped peels of citrus amanatsudaidai was added 2 to 4-fold amount of methanol, and the resulting mixture was stirred well to obtain 1.8 lit. of peel extra. This extract was filtered to remove precipitate, and the filtrate (1.7 lit.) was subjected to distillation under reduced pressure to remove the methanol and to be concentrated to dryness. The crude extract thus obtained was dissolved in 1.7 lit. of a purified water to prepare an aqueous solution, and the solution was applied to an activated carbon column The liquid passed through the column was combined with washing fractions, and the resulting mixture was applied to an adsorption column of a strong-acidity cation-exchange resin Amberlite IR-120B [H⁺]. The active fraction was eluted with a 0.5N ammonia water to give 7.66 g of crude powder.

The crude powder was subjected to cellulose column chromatography, and after the column was washed with 2 lit. each of butanol: acetic acid: water=20:1:1, 10:1:1 and 5:1:1, the active substance was eluted with 2 lit. of an eluent, butanol: acetic acid: water=3:1:1, to obtain 2.1 g of crude purified product. The crude purified product was subjected to gel filtration (developing solvent: water) using Sephadex G-25 as a carrier to obtain 1.12 g of crude purified product. The product was then subjected to cellulose column chromatography, and after the column was washed with 0.5 lit. each of ethanol: water=7.5:1 and=5:1, the active substance was eluted with 1 lit. of an eluent, ethanol: water=3:1 to 1:3, to obtain 460 mg of crude purified product. The product was further subjected to cation-exchange type high-performance liquid chromatography (developing solvent: water) to give 300 mg of peptide having actions of promoting proliferation of hair papilla cells.

Test Example 1
Effects On Hair Papilla Culture Cells of Rabbit Whiskers

Whisker hair papillae separated from a Japanese white rabbit were inoculated to a surface of a collagen (type IV)-coated dish to carry out culturing, according to a modification of the method of Katsuoka, K., et al.: Arch. Dermatol. Res., 279, 20–25 (1986), in a Dulbecco-modified Eagle medium (DMEW having 20% fetal bovine serum (FBS) and an antibiotic added thereto to obtain primary culture cells minted from the whisker hair papillae. These cells were subcultured in a 10% FBS-DMEM to obtain hair papilla culture cells. An assay was carried out in the following manner: The hair papilla culture cells were suspended in a 10% FBS-D.MM and the resulting suspension was seeded on a 96-well plate and cultured for 6 days with addition of an aqueous solution of the peptide obtained in Example 1 having a predetermined concentration twice in the meantime. Presence or absence of proliferation of the hair papilla culture cells was determined by means of MTT. The results are shown in Table 1.

TABLE 1

| Concentration of hair papilla cell proliferation promotor (μg/ml) | Proliferation promoting activity (%) |
|---|---|
| 15.6 | 186.5 ± 18.1 |
| 3.9 | 173.7 ± 24.8 |
| 1.0 | 136.2 ± 9.2 |
| 0.25 | 107.1 ± 20.7 |

It can be understood from these results that the peptide of the present invention is effective in a low concentration of 1.4 μg/ml to promote 150% proliferation of the hair papilla culture cells.

What is claimed is:

1. A preparation comprising peptides derived from citrus fruits, wherein said preparation is prepared by a method comprising:
    chopping peels of a citrus fruit,
    adding a solvent to said peels and stirring to obtain a peel extract,
    filtering said peel extract to produce a filtrate,
    distilling said filtrate under reduced pressure to remove said solvent and produce a crude extract,
    dissolving said crude extract in purified water to produce an aqueous solution and applying said solution to a chromatography column to produce a peptide mixture with hair growing activity;
    wherein said peptides have the following physicochemical properties:
        a) molecular weight: 2,000 to 4,000 (by gel filtration method)
        b) IR absorption spectrum (Kbr): as shown in FIG. 1;
        c) solubility: soluble in water, sparingly soluble in ether, benzene or chloroform;
        d) color-forming reaction: positive to ninhydrin reaction and sodium nitroprusside reaction, negative to anisaldehyde reaction, phenolsulfuric acid reaction and Dragendorff reaction;
        e) distinction of basic, neutral and acidic properties: neutral;
        f) water-white crystals or white crystalline powder with a slight odor; and
        g) contains aspartic acid and oxylysine.

2. The preparation according to claim 1, wherein said chromatography column is selected from the group consisting of an activated charcoal chromatography column, a cation exchange column, a cellulose chromatography column, a gel filtration column, and cation exchange type high performance liquid chromatography column.

3. The preparation according to claim 2, wherein said preparation is further purified using a further chromatography column selected from the group consisting of an activated charcoal chromatography column, a cation exchange column, a cellulose chromatography column, a gel filtration column, and cation exchange type high performance liquid chromatography column.

4. The preparation according to claim 1, wherein said peptides contain phosphoserine, aspartic acid, serine, glutamic acid, glycine, alanine, valine, cystine, methionine, oxylysine, ornithine, lysine and histidine.

5. The preparation according to claim 1, further comprising aloe.

6. The preparation according to claim 3, further comprising aloe.

7. The preparation according to claim 4, further comprising aloe.

8. The preparation according to claim 1, wherein said citrus fruit is citrus amanatsudaidai.

9. The preparation according to claim 1, wherein said solvent is methanol.

10. A method for promoting the proliferation of hair papilla cells comprising applying a preparation comprising peptides derived from citrus fruits to hair papilla cells, wherein said preparation is prepared by the following steps:
    chopping peels of a citrus fruit,
    adding a solvent to said peels and stirring to obtain a peel extract,
    filtering said peel extract to produce a filtrate,
    distilling said filtrate under reduced pressure to remove said solvent and produce a crude extract,
    dissolving said crude extract in water to produce an aqueous solution and
    applying said solution to a chromatography column to produce a peptide mixture which promotes the proliferation of hair papilla cells;
    wherein said peptides have the following physicochemical properties:

a) molecular weight: 2,000 to 4,000 (by gel filtration method)
b) IR absorption spectrum (Kbr): as shown in FIG. 1;
c) solubility: soluble in water, sparingly soluble in ether, benzene or chloroform;
d) color-forming reaction: positive to ninhydrin reaction and sodium nitroprusside reaction, negative to anisaldehyde reaction, phenolsulfuric acid reaction and Dragendorff reaction;
e) distinction of basic, neutral and acidic properties: neutral;
f) water-white crystals or white crystalline powder with a slight odor; and
g) contains aspartic acid and oxylysine.

11. The method according to claim 10, wherein said chromatography column is selected from the group consisting of an activated charcoal chromatography column, a cation exchange column, a cellulose chromatography column, a gel filtration column, and a cation exchange type high performance liquid chromatography column.

12. The method according to claim 10, wherein said solvent is methanol.

13. The method according to claim 10, wherein said citrus fruit is citrus amanatsudaidai.

14. A method for promoting the growth of hair, comprising applying a preparation containing peptides derived from citrus fruits to a patient in need of such treatment, wherein said preparation is prepared by a method comprising:

chopping peels of a citrus fruit, adding a solvent to said peels and stirring to obtain a peel extract, filtering said peel extract to produce a filtrate, distilling said filtrate under reduced pressure to remove said solvent and produce a crude extract, dissolving said crude extract in water to produce an aqueous solution, and applying said solution to a chromatography column to produce a peptide mixture with hair growing activity;

wherein said peptides have the following physicochemical properties:
a) molecular weight: 2,000 to 4,000 (by gel filtration method)
b) IR absorption spectrum (Kbr): as shown in FIG. 1;
c) solubility: soluble in water, sparingly soluble in ether, benzene or chloroform;
d) color-forming reaction: positive to ninhydrin reaction and sodium nitroprusside reaction, negative to anisaldehyde reaction, phenolsulfuric acid reaction and Dragendorff reaction;
e) distinction of basic, neutral and acidic properties: neutral;
f) water-white crystals or white crystalline powder with a slight odor; and
g) contains aspartic acid and oxylysine.

15. The method according to claim 14, wherein said chromatography column is selected from the group consisting of an activated charcoal chromatography column, a cation exchange column, a cellulose chromatography column, a gel filtration column, and a cation exchange type high performance liquid chromatography column.

16. The method according to claim 14, wherein said solvent is methanol.

17. The method according to claim 14, wherein said citrus fruit is citrus amanatsudaidai.

* * * * *